(12) United States Patent
Deckman et al.

(10) Patent No.: US 7,270,792 B2
(45) Date of Patent: Sep. 18, 2007

(54) PROCESS FOR PRODUCING PARA-XYLENE

(75) Inventors: Harry W. Deckman, Clinton, NJ (US);
Ronald Richard Chance, Annandale, NJ (US); James Alexander McHenry, Washington, NJ (US); John Di-Yi Ou, Houston, TX (US); Juan José Reinoso, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 348 days.

(21) Appl. No.: 11/038,827

(22) Filed: Jan. 18, 2005

(65) Prior Publication Data

US 2005/0165265 A1    Jul. 28, 2005

Related U.S. Application Data

(62) Division of application No. 09/791,300, filed on Feb. 22, 2001, now Pat. No. 6,878,855.

(60) Provisional application No. 60/184,010, filed on Feb. 22, 2000.

(51) Int. Cl.
*B01J 7/02* (2006.01)
*B01D 11/04* (2006.01)
*C07J 5/22* (2006.01)

(52) U.S. Cl. ............... 422/236; 422/255; 422/256; 422/261; 585/477; 585/478; 585/481; 585/828

(58) Field of Classification Search ............... 422/236, 422/255, 256, 261; 585/477, 478, 481, 828
See application file for complete search history.

(56) References Cited

U.S. PATENT DOCUMENTS

| 3,518,206 A | 6/1970 | Sowards et al. |
|---|---|---|
| 3,662,013 A | 5/1972 | Machell et al. |
| 3,706,812 A | 12/1972 | de Rosset et al. |
| 3,729,523 A | 4/1973 | Grandio, Jr. et al. |
| 3,732,325 A | 5/1973 | Pharis et al. |
| 4,120,911 A | 10/1978 | Davidson |
| 4,236,996 A | 12/1980 | Tabak et al. |
| 4,886,929 A | 12/1989 | Neuzil et al. |
| 4,899,011 A | 2/1990 | Chu et al. |
| 5,122,357 A | 6/1992 | Bedard et al. |
| 5,863,315 A | 1/1999 | Jullian et al. |
| 5,925,800 A | 7/1999 | Sun et al. |

FOREIGN PATENT DOCUMENTS

WO    96/35498    11/1996

*Primary Examiner*—Thuan Dinh Dang
(74) *Attorney, Agent, or Firm*—Michael Kerns; Xiaobing Feng

(57) ABSTRACT

A process and a system for increasing para-xylene production from a $C_8$ aromatic feedstream by coupling at least one xylene isomerization reactor with at least one pressure swing adsorption unit or temperature swing absorption unit to produce a product having a super-equilibrium para-xylene concentration. This product is then subjected to para-xylene separation and purification.

14 Claims, 4 Drawing Sheets

PROCESS FOR PRODUCING PARA-XYLENE

CROSS-REFERENCE TO RELATED APPLICATIONS

This application is a divisional of U.S. Application Ser. No. 09/791,300 filed Feb. 22, 2001 now U.S, Pat. No. 6,878,855; which claims priority from provisional patent application Ser. No. 60/184,010, filed Feb. 22, 2000, which is fully incorporated herein by reference.

BACKGROUND OF THE INVENTION

1. Field of the Invention

This invention relates to a process and a system for increasing para-xylene recovery and production from a hydrocarbon feedstream comprising $C_8$ aromatics. In particular, the process and the system comprise xylene isomerization and pressure swing adsorption to form a desorption effluent comprising a para-xylene enriched product. Para-xylene is then recovered from this desorption effluent.

2. Description of the Related Art

Ethylbenzene (EB), para-xylene (PX), ortho-xylene (OX) and meta-xylene (MX) are often present together in a typical industrial $C_8$ aromatic product stream from a chemical plant or a refinery. For instance, commercially available Mobil Selective Toluene Disproportionation and Mobil Toluene Disproportionation processes may produce such a stream. Naphtha reforming plants also produce these aromatics. Commercial examples include POWERFORMING and PLATFORMING processes. It is also possible to convert $C_3/C_4$ hydrocarbons into aromatics via a CYCLAR process. These $C_8$ aromatics are also produced in large quantities in oil refineries, which produce gasoline, diesel fuel, heating oil, and other fuels. Benzene and toluene, having lower molecular weights than the $C_8$ stream, are two other large volume valuable aromatic products produced from some of these chemical plants and refineries. (PLATFORMING and CYCLAR are registered trademarks of UOP, Inc.)

Among the four $C_8$ aromatic compounds related to the present invention, all having the same molecular formula $C_8H_{10}$, EB is used primarily for making styrene by direct dehydrogenation, oxidative dehydrogenation, or conversion via an ethylbenzene hydroperoxide intermediate, a co-product from an "Oxirane" process for producing propylene oxide. Styrene is a large volume monomer for producing many important polymers such as polystyrene and styrene-butadiene rubbers. However, largely for economic, logistic, production control and product purity reasons, most EB feedstocks used in typical styrene production plants are produced on purpose by alkylation of benzene with ethylene, not by recovery from a $C_8$ aromatics stream from a chemical plant or an oil refinery. It is not unusual that the total amount of EB from a typical $C_8$ aromatic stream is not significant enough to justify installing additional facilities for its recovery and purification as a byproduct. Accordingly, it is often desirable, sometimes necessary, to remove, convert or otherwise dispose of EB in a most economic manner.

Of the three xylene isomers, PX has the largest commercial market. PX is used primarily for manufacturing purified terephthalic acid (PTA) and terephthalate esters such as dimethyl terephthalate (DMT), which are used for making various polymers such as poly(ethylene terephthalate), or PET, poly(propylene terephthalate), or PPT, and poly(butene terephthalate), or PBT. Different grades of PET are used for many different popular consumer goods such as films, synthetic fibers, and plastic bottles for soft drinks. PPT and PBT may be used for making similar products with different properties.

While OX and MX are also useful as solvents or raw materials for making products like phthalic anhydride and isophthalic acid respectively, demands for OX and MX and their downstream derivatives in the market place are much smaller and more limited. Because of the much higher demand for PX as a feedstock than the demands for OX and MX, it is usually more desirable commercially to increase or even maximize PX production from a particular source of $C_8$ aromatic materials. Otherwise, there could be substantial overproduction of MX and/or OX and inadequate production of PX, thus creating an imbalance of supplies and demands in the various $C_8$ aromatics markets.

There are two major technical challenges in achieving this goal of increasing or maximizing PX yield and/or production from a particular process or plant. First, the $C_8$ aromatics are difficult to separate due to their similar chemical structures and physical properties and identical molecular weights. Second, the four $C_8$ aromatic compounds, particularly the three xylene isomers, are usually present in concentrations dictated by the thermodynamics of production of the $C_8$ aromatic stream in a particular plant or refinery. As a result, the PX production is limited, at most, to how much PX is originally present in the $C_8$ aromatic stream unless additional processing steps are used to increase the amount of PX and/or to improve the PX recovery efficiency. Therefore, increasing the PX yield and improving the PX production efficiency by using different and novel technologies or processes are two objectives constantly sought after by the chemical and refining industries and the technology community.

Fractional distillation is a commonly used method for many processes in many industrial plants to separate chemicals. However, it is often difficult to use such a conventional fractional distillation technology to separate the EB and different xylene isomers efficiently and economically. This is because the boiling points of the four $C_8$ aromatics fall within a very narrow 8° C. range, from about 136° C. to about 144° C. (see Table I). The boiling points of PX and EB are about 2° C. apart. The boiling points of PX and MX are only about 1° C. apart. As a result, large equipment, significant energy consumption, and/or substantial recycles would be required to provide effective and satisfactory xylene separations.

TABLE I

| $C_8$ compound | Boiling Point (° C.) | Freezing Point (° C.) |
| --- | --- | --- |
| ethylbenzene (EB) | 136 | −95 |
| para-xylene (PX) | 138 | 13 |
| meta-xylene (MX) | 139 | −48 |
| ortho-xylene (OX) | 144 | −25 |

Notwithstanding, various methods and processes, other than simple fractional distillation, to separate these $C_8$ aromatic components into individual products have been tested and developed, and some are successfully practiced in commercial scales. Examples include fractional crystallization, adsorption, and combinations thereof.

Fractional crystallization in a crystallizer takes advantage of the differences between the freezing points and solubilities of the $C_8$ aromatic components at different temperatures. Due to its relatively higher freezing point, PX is usually separated as a solid in such a process while the other components are recovered in a PX-depleted filtrate. High PX purity, a key property needed for satisfactory conversion of PX to PTA and/or DMT commercially in most plants, can be obtained by this type of fractional crystallization. U.S. Pat. No. 4,120,911 provides a description of this method. A crystallizer that may operate in this manner is described in U.S. Pat. No. 3,662,013. Commercially available processes and crystallizers include crystallization isofining process, continuous countercurrent crystallization process, direct $CO_2$ crystallizer, and scraped drum crystallizers. Due to high utility usage and the formation of a eutectic between PX and MX, it is usually more advantageous to use a feed with as high an initial PX concentration as possible when using fractional crystallization to recover PX.

A different xylene separation method uses molecular sieves, such as zeolites, to selectively adsorb para-xylene from the $C_8$ aromatic feedstream to form a PX-depleted effluent. The adsorbed PX is then desorbed by various ways such as heating, stripping, and others. (See generally U.S. Pat. Nos. 3,706,812, 3,732,325 and 4,886,929) Two commercially available processes used in many chemical plants or refineries are PAREX and ELUXYL processes. Both processes use molecular sieves to adsorb PX. In such molecular-sieve based adsorption processes, a higher amount of PX, typically over 90%, compared with that from a fractional crystallization process, typically below 65%, may be recovered from the PX present in a particular feed. (PAREX is a registered trademark of UOP Inc.; ELUXYL is a registered trademark of Institut Francais du Petrole).

Depending on the effectiveness of a particular separation method or system, these PX depleted streams or filtrates may still contain various amounts of residual PX. At the same time, MX, OX and EB concentrations are higher than those in the original $C_8$ aromatic feedstocks. The actual EB concentration may vary substantially, depending primarily on (a) the separation method, (b) the feedstock composition and (c) the isomerization catalyst and the isomerization conditions in the isomerization reactor when the PX-depleted streams are passed or recycled through one or more xylene isomerization steps.

For many of these PX separation processes, the higher the original PX concentration in the feedstream is, the easier, more efficient and more economical it becomes to perform the PX separation. Therefore, there are strong economic and technical incentives to increase the PX concentration in a hydrocarbon feedstream comprising the $C_8$ aromatic compounds prior to sending the feedstream to a PX separator such as a PAREX unit or a fractional crystallizer discussed above.

As discussed in the preceding paragraphs, PX may be separated by different methods such as fractional crystallization or selective adsorption. Without additional processing steps, however, the total amount of recoverable PX is still limited. This is because EB and the three xylenes are usually present in concentrations close to those dictated by the thermodynamic conditions under which they are produced, due to their inter-convertibility under such production conditions. It is not unusual that the PX concentration is not more than about 25 mol % (equivalent to 25 wt %), and MX, at about 50 mol %, of the total $C_8$ aromatics present in a typical aromatic product stream produced in a refinery or a chemical plant. Thus, many industrial aromatic processes provide additional steps to recycle and to isomerize the various PX depleted streams coming from the separation step to produce more PX by isomerizing OX, MX and sometimes EB to PX.

Due to its chemical properties, EB may be destroyed partially or completely under certain xylene isomerization conditions. As discussed later, when EB is destroyed during xylene isomerization, it is usually converted into benzene and ethane in the presence of and with consumption of hydrogen. Due to their very different physical and chemical properties, benzene and ethane can be easily separated from the xylenes by many conventional methods. With or without EB destruction, an isomerization product effluent from a xylene isomerization reaction becomes a part of the feedstream to the PX separator, such as a crystallizer or an adsorption unit.

Regardless the specific systems of and the catalysts selected for these isomerization processes, the PX concentrations in the isomerization effluents from the isomerization reactors are dictated primarily by thermodynamics, i.e. within the equilibrium concentration limits of PX under the isomerization conditions. Similar to the situation discussed earlier involving $C_8$ aromatics streams directly coming from refineries or chemical plants, it is desirable to increase the PX concentrations in the xylene isomerization effluents to levels higher than those dictated by xylene isomerization thermodynamics (super-equilibrium concentration), prior to sending the isomerization effluents, as the feeds, to PX separation units. As before, this higher PX concentration would allow better utilization and/or de-bottlenecking of the existing unit and equipment, such as a fractional crystallizer, for PX separation.

SUMMARY OF THE INVENTION

It is discovered in this invention that by coupling at least one xylene isomerization step with at least one pressure swing adsorption (PSA) step or a temperature swing adsorption (TSA) step, one can produce a PSA and/or TSA desorption product having PX in a super-equilibrium concentration, i.e. becoming PX-enriched. This super-equilibrium-concentration PX containing aromatic product is useful as a feed for further downstream fractional crystallization or other type separation processes to produce a higher yield of pure PX. EB may be destroyed in the process at the xylene isomerization step. Optionally, hydrogen may be used in the xylene isomerization reactor to improve isomerization performance.

This novel process and the associated system may be used in a grass roots plant, an existing chemical plant, an existing refinery or any relevant processes to increase or maximize the PX production capacity, the overall PX recovery and/or the PX yield from a particular $C_8$ aromatic feedstock. As an option, it is also feasible for the present invention to recycle and isomerize or destroy MX and/or OX and/or EB to near extinction, thus producing essentially only PX from a particular xylene fraction of a hydrocarbon feedstream. It will become clear from the disclosures herein that more efficient heat integration and better heat management may be achieved or fewer pieces of equipment may be required by applying certain embodiments of the present invention to aromatics production processes and systems.

The present invention relates to a process for producing a para-xylene enriched product from a feedstream comprising xylenes and ethylbenzene, the process comprises passing the feedstream through at least one isomerization reactor containing an isomerization catalyst and, optionally, under a hydrogen partial pressure, to form an isomerization effluent; and passing the isomerization effluent through a pressure swing adsorption unit or a temperature swing adsorption unit, preferably in the vapor phase, containing a sorbent to produce alternately, at a cycle time, a desorption effluent comprising the para-xylene enriched product and an exiting raffinate comprising a para-xylene depleted product. The sorbent comprises an adsorbent and, optionally, a heat absorbing medium.

It is another object of the present invention to recycle the PX-depleted exiting raffinate to become part of the feedstream going into at least one isomerization reactor to increase the PX production.

It is also an object of the instant invention to use an isomerization catalyst that can partially, substantially completely or completely destroy all of the EB present in the feedstream under the effective isomerization conditions in the isomerization reactor. If EB is absent or substantially absent in the isomerization effluent coming out of the isomerization reactor, it is within the embodiment of the present invention to pass the PX-depleted PSA or TSA exiting raffinate, also referred to as raffinate, through a second isomerization reactor at a lower temperature without the need of significant heat input to the second isomerization reactor.

The present invention further relates to a system for producing a para-xylene enriched product. The system comprises at least one xylene isomerization reactor containing an isomerization catalyst and under a hydrogen partial pressure, wherein a first para-xylene depleted feedstream is isomerized to produce a first product having para-xylene at or near an equilibrium concentration under isomerization conditions; at least one gas phase pressure-swing adsorption unit or a temperature swing adsorption unit (hereafter generically referred to as a "swing adsorption" (SA) unit) operating in cycles with a cycle time to produce from the first product, alternately, a para-xylene depleted product in an adsorption mode, including a pressurization step, and the para-xylene enriched product having a super-equilibrium para-xylene concentration in a desorption mode, including a blow-down step; and at least one para-xylene recovery unit wherein para-xylene is separated and recovered from the para-xylene enriched product. Additional steps such as purges and rinsing for the SA operation may be used.

It is also within the embodiment of the present invention to use two or more SA units, and optionally two or more isomerization reactors. In a given process or system, the SA units and the isomerization reactors may be at two or more different temperatures or operated under two or more sets of different operating conditions. It is preferred to have one of the two or more isomerization temperatures high enough to destroy all or most EB under the isomerization conditions. Different catalysts may be used in different isomerization reactors. Different sorbents or adsorbents may be used in different SA units.

Another embodiment relates to a PX-enriched product produced by a process or in a system disclosed herein.

BRIEF DESCRIPTION OF THE DRAWINGS

The present invention will be better understood and the advantages will become more apparent from the descriptions herein when read in connection with the accompanying drawings.

One having ordinary skill in the art understands that the drawings are used for illustration purposes only and they do not represent all the possible systems or process variations embodied by the present invention. In addition, the drawings do not include many pieces of equipment and apparatus and certain processing steps that may be needed for industrial, commercial or even experimental purposes. While such equipment, apparatus and steps that are not needed for understanding the essence of the present invention are not shown in the drawings, some of them may be mentioned from time to time to illustrate various aspects of the invention. It is also noted that some of the equipment, such as heat exchangers and compressors, may be placed at different places in the process or system, depending on the conditions such as temperatures and pressures in different reactors.

DETAILED DESCRIPTION OF INVENTION

Figure 1:
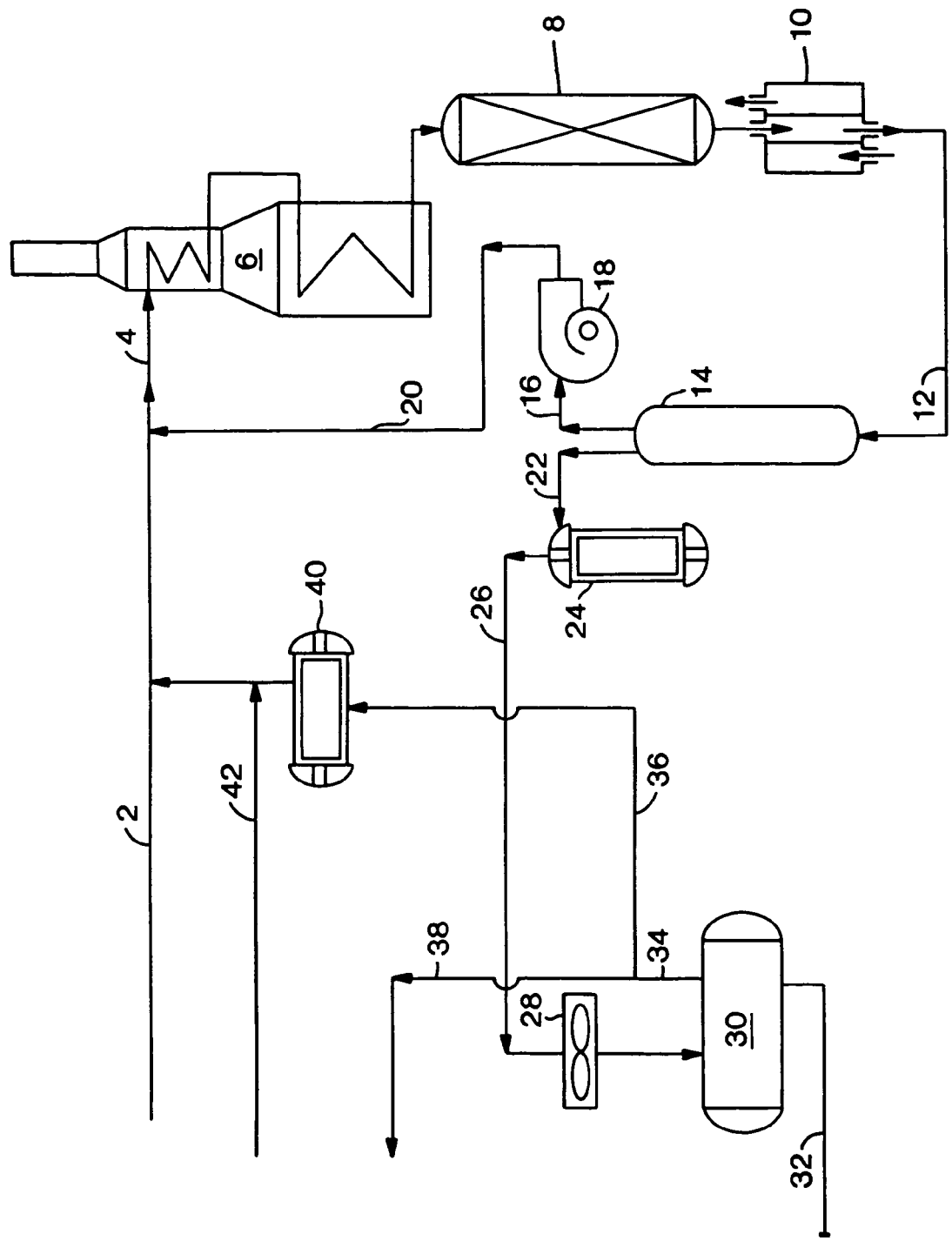
FIG. 1 depicts a schematic diagram of a process and simplified system with the associated apparatus and equipment in accordance with the present invention.

The present invention relates to a process and a system for increasing or maximizing the production, recovery, and/or yield of para-xylene (PX) in chemical plants and refineries, where $C_8$ aromatic compounds are separated, produced and/or processed. It also relates to a PX enriched product produced by such a process or in such a plant.

A process of the present invention comprises isomerizing a feedstream comprising $C_8$ aromatic compounds to produce an isomerization effluent, followed by subjecting the isomerization effluent to a swing adsorption (SA) step in the presence of an adsorbent. Unless otherwise specified, the terms "isomerization" and "xylene isomerization" are used interchangeably herein. Hereafter the process will be described with reference to a PSA unit, but it is to be understood that this discussion contemplates the use of a TSA unit as the SA unit.

A PSA unit operates in adsorption mode-desorption mode cycles with a cycle time. In the adsorption mode, there may be a pressurization step and a high pressure adsorption step. The desorption mode may include (a) a blowdown step, either co-current or countercurrent, (b) a low-pressure desorption step and optionally, (c) prior to the blowdown step, a rinse step at high pressure (such as adsorption mode pressure) to purge the adsorbent bed for higher product purity. There may be additional steps such as pressure equalization in operating a PSA unit to reduce utility usage or to obtain better results. The cycle time may be constant or variable. There also may be one or more purges within or outside each regular PSA cycle. These purges are carried out as scheduled, as needed or both.

A PX-depleted exiting raffinate is produced during the adsorption mode of PSA. During the desorption mode of PSA, a desorption stream having a super-equilibrium PX concentration is produced. Optionally, the PX-depleted exiting raffinate from a PSA unit may be sent back to become part of the feedstream to the isomerization reactor. This raffinate can also be used to purge the PSA sorbent bed to recover more PX trapped in voids of the sorbent after the desorption mode of the cycle. There may be two or more isomerization reactors operating at the same or different conditions. It is also preferred to have at least two PSA units.

If there are two or more PSA units, they may be operated under the same or different conditions.

The term "PX-depleted" only means that PX concentration is lowered in the exiting stream (raffinate) of a particular PSA unit compared to the concentration in the feedstream to the same PSA unit. It does not mean that all of PX has to be depleted or removed from the xylenes-containing feedstream(s) to the PSA unit(s).

For the present invention, the feedstream to a xylene isomerization reactor comprises PX in a concentration below its equilibrium concentration relative to other interconvertible $C_8$ aromatic compounds under the isomerization conditions. The catalyzed xylene isomerization step serves to increase the PX concentration to near its equilibrium level. Then, the isomerization effluent is fed to the PSA unit(s). The isomerization step also may serve to destroy part or all of EB present in the feedstream when the temperature is above about 350° C. In order to achieve better PX separation by PSA, the temperature in a PSA unit is typically lower than the isomerization temperature, particularly when EB destruction is desired in the isomerization step as well.

If EB destruction is fairly complete in the isomerization reactor at a first temperature, it is optional and often preferred to have another one or more xylene isomerization reactors operating at a second temperature, which is lower than the first temperature. If this second lower xylene isomerization temperature is not too different from the temperature of the coupled PSA unit, for example within ±20° C., the isomerization product from this second (the other) xylene isomerization reactor, may be sent to the PSA unit without the need of using a heat exchanger to cool the stream. In addition, the PX-depleted exiting stream from the PSA unit may be, optionally, sent back to the second xylene isomerization reactor operated at the lower (second) temperature without the need of any additional heat input through a heat exchanger. In accordance with this invention, additional PX may be produced with simplified plant operations, fewer pieces of plant equipment, and lower utility usage. MX and OX may be recycled to extinction in this manner.

Another aspect of the instant invention relates to a plant or system comprising the necessary processing units, reactors, equipment, and controls. Such processing units, reactors, equipment and controls provide the various necessary and/or optional functions of isomerizing xylenes and producing a PX enriched product by pressure swing adsorption to achieve the desired higher, maximum and/or improved PX production, recovery and/or yield. In addition, lower utility usage or fewer pieces of required equipment also may be achieved by using the embodiments of the present invention in an existing plant or a grass roots plant to increase PX production. It is also envisioned that less lower-valued products or wastes will be produced.

A desorption effluent containing a super-equilibrium PX concentration is produced during the desorption mode of PSA by passing the feedstream comprising $C_8$ aromatic compounds through at least one isomerization reactor containing a suitable isomerization catalyst and in the presence of a hydrogen partial pressure to form an isomerization effluent, followed by feeding the isomerization effluent through at least one PSA unit operating alternately between an adsorption mode producing an exiting raffinate and the desorption mode producing the desorption effluent. It is common to have two or more PSA units in the plant or system.

After a certain period of time into the adsorption mode, which is determined primarily by the capacity of the adsorbent in the PSA unit, the feedstream to the first is stopped or diverted to another PSA unit, if there are two or more PSA units, or bypassed to another tower or equipment such as a de-toluene tower. A high pressure rinse step may be carried out prior to blowdown. A desorption mode is carried out with the first PSA unit by lowering the pressure (blowdown) followed by a low-pressure desorption step to form the desorption effluent comprising a PX-enriched (super-equilibrium concentration) product.

The desorption effluent, with or without combining the effluent stream from the rinse step, is then sent to a separation unit such as a PAREX unit or a fractional crystallization unit for PX recovery and purification. After desorption, the first PSA unit may be put back into the adsorption mode. There may be one or more purges between or outside the adsorption mode and the desorption mode. In addition to and/or in place of lowering the pressure, even to vacuum, in the PSA unit to effect desorption, other ways such as increasing the temperature, desorption product purge, solvent stripping, particularly streams generated in the process such as a benzene/toluene (with or without ethane) stream and an MX-rich stream and combinations thereof may be used. The purges may be carried out in a countercurrent manner. As already discussed, an additional rinse step may be carried out as well.

A $C_8$ aromatic compound stream from a typical chemical plant or refinery comprises PX, MX, OX and EB, which are at close to thermodynamic equilibrium concentrations. Subjecting this stream to xylene isomerization will not produce significant benefits, if any at all. Accordingly, the feedstream to the isomerization reactor used for the present invention preferably comprises at least part of a PX-depleted exiting raffinate recycled from one or more PSA units so that the final PX concentration in the feedstream is lower than that dictated by thermodynamics under a set of isomerization conditions, particularly the isomerization temperature, used for the isomerization reactor. Typically, the PX concentration in this feedstream to the xylene isomerization reactor is lower than about 25 wt % of all the four $C_8$ aromatic compounds present in the stream.

In addition to xylenes and ethylbenzene, the $C_8$ aromatic feedstream may also contain certain amounts of other aromatic or even non-aromatic compounds. Examples of such aromatic compounds are benzene, toluene and $C_9$ aromatics such as mesitylene, pseudo-cumene and others. Because of the differences in molecular weights, boiling points and other physical and chemical properties, these other compounds, aromatic or non-aromatic, can be separated relatively easily from the xylenes and EB. As understood by a person having ordinary skill in the art, these compounds do not present significant problems for most xylene production processes or facilities. Accordingly, different processing units, reactors, apparatus, equipment, and controls for effecting their separations are substantially left out of the drawings of FIG. 1 and FIG. 2.

There are many catalysts or combinations of catalysts that can be used in a xylene isomerization reactor to effect the desired isomerization reaction. There are generally two types of xylene isomerization catalysts. One type of isomerization catalysts can more or less equilibrate the four different $C_8$ aromatic compounds, including EB, to the concentrations dictated by thermodynamics under the reaction conditions. This allows maximum formation of PX from $C_8$ aromatics in a particular feed. Examples of these type catalysts include IFP/Engelhard Octafining and Octafining II catalysts used in the respective processes.

The other type of xylene isomerization catalysts can effect EB destruction too, preferably in the presence of hydrogen. As discussed earlier, this type process, plant and catalysts will remove EB and produce benzene and ethane as byproducts. This may be a desirable disposition of EB, depending on supplies and demands of various products as well as other equipment present in a particular plant. Examples include Mobil High Temperature Isomerization (MHTI) catalysts, Mobil High Activity Isomerization catalysts (MHAI) and UOP ISOMAR I-100 catalysts used in the respective processes. (ISOMAR is a registered trademark of UOP, Inc.)

A number of suitable isomerization reactors may be used for the present invention. Some non-limiting examples are described in U.S. Pat. Nos. 4,899,011 and 4,236,996.

The xylene isomerization reactions may be carried out under various effective conditions and in many different systems. Such effective conditions include a wide temperature range. Because it is generally known and/or believed that the PX equilibrium concentration among the xylenes is not strongly temperature dependent within the range suitable for the present invention, the selection of a particular temperature for a particular isomerization reactor would not have substantial impact on the PX recovery or yield. However, the selection of a particular isomerization reaction temperature in a particular reactor of the process or system, does depend on many factors or considerations, such as whether there is EB in the feed, whether it is desirable to destroy EB in the feed during isomerization, whether there are two or more isomerization reactors, what the operating temperature in the PSA unit is and combinations thereof.

The temperature range for xylene isomerization is in the range of from about 200° C. to about 550° C., preferably from about 250° C. to about 520° C. and more preferably from 325° C. to about 450° C. With most, if not all, known catalysts, EB destruction does not occur to any significant extent until the reaction temperature reaches about 300° C., preferably about 325° C. It is therefore preferred to operate at a temperature higher than about 325° C. within the above temperature ranges in order to destroy EB. If there are two or more xylene isomerization reactors used for a process or a system, it is preferred to have one reactor operating at a first temperature in the above temperature ranges and the other, operating at a temperature lower than the first temperature. Such a lower temperature is preferred to be in the range of from about 200° C. to about 350° C. and more preferably from about 220° C. to about 300° C.

If there is no EB in the feedstream to a particular isomerization reactor or if EB destruction is not needed or preferred, lower isomerization temperatures may be used for the purposes of reducing energy consumption and utility usage. It may be more preferable to match the temperature of the isomerization reactor with the temperature of the PSA unit to minimize requirements of heat exchange and/or heat exchange equipment. A PSA unit is typically operated at a temperature lower than that in a xylene isomerization reactor with concomitant EB destruction.

For the present invention, a xylene isomerization reaction may be carried out in a liquid phase, a vapor (gas) phase, a super critical phase, or a combination thereof. The selection of isomerization reaction conditions and the specific composition of the aromatic feedstream being isomerized determine the physical state of the aromatic feedstream in a xylene isomerization reactor. Because there is at least one PSA unit coupled with the isomerization reactor and that the PSA unit(s) of this invention preferably operates in the vapor phase, it is more advantageous to operate the isomerization reaction in the vapor phase as well. This would streamline and simplify process or plant operations, either commercial or experimental, and to eliminate certain equipment such as heat exchangers from such process or plant.

It is also within the embodiment of the present invention to use an isomerization catalyst, system, or other ways that also could either isomerize and/or destroy EB during the isomerization step. As discussed earlier, while EB is a useful raw material for such important monomer as styrene, sometimes it may not be economical to recover a relatively small quantity of EB in an aromatic chemical plant. As a result, it may be more desirable operationally and economically, thus preferred, to use suitable reaction conditions, particularly higher temperatures, in the presence of a suitable isomerization catalyst that is also capable of effecting the desired EB destruction at the same time. EB can be dealkylated to form benzene and ethylene at a temperature higher than about 300° C. under many reaction conditions. In the presence of hydrogen, preferred for the present invention, EB is primarily converted to benzene and ethane via a hydro-dealkylation reaction. For each mole of EB destroyed in this manner, one mole of hydrogen is consumed in accordance with reaction stoichiometry. Accordingly, it is more preferred to use hydrogen in a molar amount at least equal to the moles of EB to be converted in a particular feedstream in the isomerization reactor.

It is further within the embodiment of the present invention to have at least one isomerization reactor operating at a temperature high enough to destroy most EB. This becomes a low or no EB case discussed earlier. Accordingly, it is optional and preferred that the PX-depleted exiting raffinate produced in the adsorption mode from a PSA unit, which is coupled to the high temperature xylene isomerization reactor, is sent to a second different, lower temperature isomerization reactor to further isomerize MX and OX in the exiting raffinate into more PX. Then, this re-equilibrated PX-containing mixture can be sent to the same or a different PSA unit for making PX-enriched products. In this mode, it is optional to use different catalysts in different isomerization reactors, if desirable.

It is optional to recycle MX and OX to extinction within the process or plant. For the isomerization step of the process and system, a total pressure in the reactor, including all hydrocarbons and any other gases or vapors such as hydrogen present in the xylene isomerization reactor, is in the range of from about 200 kPa to about 6 MPa, preferably from about 300 kPa to about 3 MPa and more preferably from about 400 kPa to about 1 MPa. A suitable partial pressure of hydrogen in the isomerization reactor is in the range of from about 50 kPa to about 6 MPa, preferably from about 100 kPa to about 3 MPa. A suitable partial pressure of xylenes and ethylbenzene in the isomerization reactor is in the range of from about 100 kPa to about 6 MPa, preferably from about 200 kPa to about 3 MPa.

While not required by the xylene isomerization reaction itself, it is found to be beneficial and preferred to have at least some hydrogen at a suitable partial pressure in the isomerization reactor. For instance, hydrogen has been shown to improve the cycle and/or ultimate life of the isomerization catalyst before it has to be replaced or regenerated. It is generally believed that hydrogen will reduce coking, i.e. deposit of carbonaceous materials, on the isomerization catalyst. As discussed earlier, hydrogen is needed, in at least equal-molar quantity to EB, for EB destruction by dealkylating EB to form ethane and benzene.

The hydrogen to C8 aromatics molar ratio (also referred to as $H_2$/oil ratio) can be in a wide range from about 0.1 to 100 moles of hydrogen to 1 mole of xylenes. It is preferred to have a molar ratio in the range of from about 0.5 to about 2 moles of hydrogen to 1 mole of xylenes, more preferably from about 0.8 to about 1.2, and most preferably from about 0.9 to about 1.1. In a typical industrial operation, it is usually convenient as well as beneficial to keep the hydrogen partial pressure at about or slightly less than half of the total pressure in a particular isomerization reactor. One having ordinary skill in the art understands that in the vapor phase, these molar ratios are the same as (assuming idea gas laws are followed) or close to the ratios of the respective partial pressures of the components.

The hydrogen pressure may be changed or adjusted in different isomerization reactors if there is more than one in a particular process or system. In addition, there may be a need to balance hydrogen pressures or concentrations and/or to prevent hydrogen buildup in various parts of the entire process or system, including the PSA unit(s) and any recycle streams. Hydrogen may be produced, for instance, when coke is formed or when other unintended and/or undesired dehydrogenation reaction takes place. All these can be accomplished by purging and/or providing hydrogen make-up at certain point(s) of a process or system, or other methods known to those skilled in the art.

The WHSV (weight hourly space velocity) flow rate of total hydrocarbons in the feed, including all the aromatics, over the catalyst in the xylene isomerization reactor is in the range of from about 0.5 to 20 $h^{-1}$. The flow rate is determined on a weight-to-weight basis.

As described herein, in a process or system of the present invention at least one PSA step or unit is coupled to at least one xylene isomerization step or reactor to produce from the isomerization effluent a desorption PX-enriched effluent (infra) containing a super-equilibrium PX concentration, i.e. a concentration higher than equilibrium concentration dictated by thermodynamics. Such a PX super-equilibrium concentration in the PX-enriched product means a PX concentration in the range of from about 28 wt % (or equivalent to 28 mole %) to about 80 wt % of all the four $C_8$ aromatics, EB, OX, MX and PX, present in a desorption effluent from a PSA unit.

SA is a cyclic high pressure adsorption/low pressure desorption method in the presence of one or more suitable sorbents, which comprise one or more adsorbents and, optionally, one or more heat absorbing media. It is a way of separating different components in a vapor or gas phase provided that at least two components have different adsorption characteristics under the different conditions, particularly different pressures. Other conditions, if beneficial, such as temperature may be changed during the desorption mode as well.

In a typical PSA unit or any other PSA type processing equipment suitable for making a PX enriched product having a super-equilibrium PX concentration, a mixture of xylene gases or vapors, optionally with some hydrogen, is brought into contact with a suitable sorbent in the PSA unit at a high pressure. There may be a pressurization step prior to the adsorption step. This is the adsorption mode. At least one component, PX for the present invention, in the mixture may exhibit higher affinity to the adsorbent part of the sorbent than the others (MX, OX, EB etc), thereby becoming selectively adsorbed by the adsorbent. The preferentially adsorbed component, PX, then becomes partially or totally depleted in the exiting raffinate exiting the PSA unit during the adsorption mode of the cycle, thus effecting a desired partial or full separation between the selectively adsorbed component, PX, and the rest in the mixture.

The adsorption continues until the capacity of the adsorbent is reached. Depending on the component adsorbed, the type of separation and operational criteria defining a successful separation, the capacity of a particular adsorbent is considered to have been reached for a particular component, PX, when one or more of the following is observed in the exiting raffinate: (a) PX is detected; (b) concentration of PX becomes higher than a pre-determined acceptable level; and (c) concentration of PX becomes the same as that in the feedstream.

A sorbent used in the PSA unit is selected to effect a particular separation. As discussed above, the sorbent comprises one or more adsorbents and, optionally or preferably one or more heat absorbing media. Many zeolites, both natural and synthetic, have been used as the adsorbent in PSA units to separate nitrogen from oxygen in the air. Others such as zeolite 5A, erionite and chabazite have been disclosed in U.S. Pat. No. 5,863,315 for separating various n-paraffins from aromatic compounds.

Many different compounds and their mixtures have been found suitable for use as an adsorbent for the PSA step of the present invention to separate $C_8$ aromatic compounds. One important criterion is that a suitable adsorbent must have an acceptable capacity for PX under the conditions in the adsorption mode. A "capacity" is expressed herein as weight %—the ratio of the weight of PX adsorbed per 100 weights of the adsorbent used under a particular set of conditions. For process economics and operating efficiency reasons, the higher the capacity of the adsorbent for PX, the better. Although even lower capacities may be used, it is generally better to have at least about 0.1 wt % PX capacity under the operating conditions of the present invention. It is preferable to have a PX capacity of 0.5 wt % or higher, more preferable to have a capacity of 1 wt % or higher. When structured sorbents are used, adsorbents with low capacities may be acceptable, particularly with fast or rapid cycles.

In addition to the adsorption capacity of an adsorbent, the adsorption and desorption kinetics are also very important factors. It is known that the time needed to reach the adsorbent capacity may vary substantially, depending on the relative concentrations (partial pressure) of the $C_8$ aromatic compounds and other competing materials in the feed, the relative and competitive adsorption affinities of the $C_8$ aromatic compounds and other competing materials, the operating conditions such as temperature and pressure, flow rates of the feedstream, adsorption kinetics and diffusion rates of PX and other components. Desorption kinetics will determine largely how long the PSA needs to stay in the desorption mode. The desorption temperature and pressure as well as whether there is any stripping compound used have substantial influence on desorption kinetics.

The sorbent may consist essentially of a structured sorbent, wherein the adsorbent and, optionally, a suitable heat absorbing medium, are placed on structured supports such as monolith supports. The support may be made from a large number of materials, such as silica, mullite, zirconia, alumina, titania, magnesia, metals such as steel and mixtures thereof. The support may be oriented or not oriented. The support may be shaped as honeycomb, sponge, screens, coils. The supports also may be coated with other materials such as colloidal silica spherulites first. To the extent they disclose and describe such supports, U.S. Pat. Nos. 5,925,800 and 3,518,206 are incorporated herein by reference. Structured sorbents can typically allow one to use very short adsorption-desorption cycles without very high pressure drops. These are sometimes referred to as fast or rapid-cycle PSA processes.

To form a structured sorbent, the total amount of an adsorbent or a sorbent comprising the adsorbent and the optional beat absorbing medium on the support is in the range of from about 0.01 wt % to 70 wt %, based on the weight of the support.

After operating in the adsorption mode for a certain period of time or until the capacity of the adsorbent is reached, the flow of the isomerization effluent from the isomerization reactor is stopped, diverted to another PSA unit, bypassed to a de-toluene tower or another suitable processing equipment or unit in the plant, and combinations thereof. The PSA unit is switched to a desorption mode. There is usually a blowdown step whereby the pressure of the PSA unit is lowered, followed by a low-pressure desorption step. Desorption of the preferentially adsorbed component, PX, may be effected by various ways such as depressurization, evacuation (to pressures lower than atmospheric pressures), low pressure stripping, or simple stripping. Depressurization (lowering the pressure) to desorb PX is preferred for the present invention.

This desorption step of the PSA desorption mode is sometimes also referred to as the regeneration step, particularly when the adsorbed components are impurities or other undesired materials to be removed. Once the adsorbent is "regenerated", the flow of the feedstream, a xylene isomerization effluent, is resumed for the adsorption mode unless a purge is performed. In the present invention, the time period going through a complete adsorption-desorption cycle is referred to as a cycle time. A more detailed definition is given below. One or more purges of the PSA unit or other associated equipment using a different gas or liquid material between the adsorption and the desorption steps also may be carried out for each cycle or as needed. The purges may help remove undesirable buildups of various products.

It is also within the scope of the present invention to have a purge step after the desorption mode and prior the adsorption mode. This is a step whereby the adsorbent is purged with a stream to recover more PX primarily left or trapped in the bed void space. This is usually carried out in the same direction of the flow of the feedstream during adsorption. The stream may be a fluid low in PX concentration. One such fluid comprises the PX-depleted exiting raffinate.

The effectiveness of a PSA for a particular separation depends on the selected adsorbent, the selected sorbent, the mechanism of adsorption, the composition of the feedstream, the absolute and relative concentrations of various $C_8$ aromatic components and other compounds present, the equipment used, the operating conditions, the desired throughput operating conditions and others. Because of the possibilities of having many different components in a particular $C_8$ aromatic feedstream, the effectiveness could vary substantially.

While not intended or preferred, it is also noted that the present invention may operate satisfactorily in the presence of small amounts of liquid in the system. A liquid may be present somewhere within the system for many reasons such as atomization, entrainment, local cooling effect, capillary phenomenon (for example, in or on the adsorbent), overpressurization or a combination thereof.

It is optional, in many cases preferred, to use two or more PSA units in order to have the reactors operated alternately or in certain prescribed sequences in the adsorption, desorption or purge (if needed) mode. This will increase the PX recovery efficiency and/or provide smoother operability of a particular process. Various schemes and systems can be devised to control many PSA units used in a single process. One example of such a scheme to separate a mixture of light paraffins (alkanes) is described in U.S. Pat. No. 5,863,315. It is preferred to use at least two PSA units for the present invention.

Because the adsorption mode is usually exothermic, it is sometimes advantageous to use an inert or substantially inert heat absorbing medium in a PSA unit to manage or control heat transfer, heat distribution and/or temperature. As the component that is being removed is adsorbed while the bed is on-line, the adsorption process will generate heat of adsorption causing a heat pulse to progress downstream through the adsorbent. It is desirable and preferred to avoid local hot spots and/or a large temperature gradient in a PSA unit. The heat absorbing medium may be gaseous, liquid, or solid. In order to minimize downstream separation and product contamination problems, it is more convenient and thus preferred for the present invention to use a solid heat absorbing medium or mixtures of different heat absorbing media.

For example, aluminum particles may be mixed with the selected adsorbent(s) to form a suitable mixture to be placed in a PSA unit. This mixture may exhibit a more uniform temperature profile, fewer hot spots, smaller temperature gradient and better temperature control during the both the adsorption and the desorption modes of the cycle. Other such suitable solid media include, but are not necessarily limited to silicon carbide, carborundum, graphite, tungsten carbide, and mixtures thereof as well as with aluminum particles. These materials are typically inert to xylenes and EB and possess high heat capacity and/or high thermal conductivity.

As already described earlier, a sorbent in the present invention comprises one or more adsorbents and, optionally or preferably, one or more heat absorbing media discussed above. There may be other components in a sorbent, if desirable. In addition, the sorbent may be placed on structured supports to carry out fast or rapid-cycle processes with very short cycle times.

When a heat absorbing medium or mixture is used as the sorbent, the amount used relative to that of the adsorbent itself (such as MFI or silicalite type zeolites) in the PSA is in the range of from about 100:1 to about 1:100, preferably from about 1:10 to about 10:1, more preferably from about 1:9 to about 1:1, all by volume ratios. Using too little of a heat absorbing medium in a PSA unit would not impart sufficient desirable effects on heat management, heat transfer or temperature control. On the other hand, using too much of such a non-adsorbing material will necessarily decrease the capacity, thus the PX throughput, of a particular PSA unit on a volume basis because too much adsorbent is necessarily displaced. Otherwise, a much larger reactor may be needed at the expense of higher capital investment. It is also within the embodiment of the present invention to select and use an adsorbent having beneficial heat absorbing properties. If the sorbent is placed on a structured support, similar volume ratios of the adsorbent to the heat absorbing medium may be used. In all of the cases, there may be other components in the sorbent composition.

In a typical PSA operation, the isomerization effluent from a xylene isomerization reactor, including some hydrogen, is brought into contact with an adsorbent in a PSA unit. During the adsorption mode, the effluent coming out of the PSA unit is referred to as an exiting raffinate (infra, and see FIG. 1 and FIG. 2). The exiting raffinate is a PX-depleted stream. Depending primarily on process economics and downstream separation facilities, PX may be substantially or only partially depleted in the PSA unit(s) of a particular process. It is sometimes referred to as a "break-through point" when the capacity of the adsorbent is "reached" or saturated and some undesirable level of PX is detected in the exiting raffinate.

The adsorption mode continues until the break-through point of the system is reached. Then, the feeding of the isomerization effluent is stopped or diverted to another PSA unit, if there is one in the process or system. The saturated PSA unit is switched to a desorption mode. Depending on the cycle time and other considerations, there could be two or a plurality of PSA units in a particular process or system for PX production.

A para-xylene enriched (i.e. having a super-equilibrium PX concentration) product, as part of a desorption effluent, is recovered during a desorption mode following the blow-down step of the PSA unit. For the present invention, the pressure of the PSA unit during the desorption mode, with a possible exception of the optional rinse step, is always lower than that during the adsorption mode. Simply by lowering the pressure of the PSA unit one can effect the desired desorption in most cases for the present invention. It is possible to facilitate or enhance the desorption by raising the PSA unit temperature, purging with a solvent/gas, or a combination thereof (pressure, temperature and purges).

Because there is usually hydrogen in the desorption effluent, it is necessary to separate hydrogen from the hydrocarbons somewhere in the process. One way to separate hydrogen from the xylenes in a desorption effluent is by feeding the desorption effluent, comprising hydrogen, PX in super-equilibrium concentration, MX and others into a compressor to increase the pressure to a level high enough to separate hydrogen and all the xylenes by gas/liquid equilibrium in a recovery drum. (For example, see FIGS. 1 and 2) The same method can be used to remove all or part of the hydrogen in the PX-depleted exiting raffinate during the adsorption mode of operation, if necessary.

Some non-limiting examples of suitable adsorbents for the present invention include zeolitic (zeolites) and non-zeolitic molecular sieves, pillared clays, carbons, and mixtures thereof. Preferred zeolites include medium pore zeolites of the MFI type, such as ZSM-5, silicalite, and others, which have a pore diameter of smaller than about 7 Å. Large pore zeolites including mordenite and faujasites, such as zeolite X and zeolite Y, with pore diameter greater than about 7 Å also may be used with or without modifications described below. Zeolites with pores smaller than about 4 Å are not preferred.

Suitable non-zeolitic molecular sieves for use as adsorbents include silicoaluminophosphates (SAPO), aluminophosphates (ALPO), substituted SAPO, substituted ALPO, and mixtures thereof. Examples include ALPO-11, SAPO-11 etc. Large pore (7 Å or larger) non-zeolitic molecular sieves may be used with or without modifications detailed below. Again, it is preferred to have pore diameter greater than about 4 Å. Pillared clays with layer distances greater than about 5 Å are preferred. Suitable carbons include activated carbons, graphite, charcoals, and mixtures thereof.

To alter or enhance their capacities, adsorption kinetics and other properties related to adsorption, all such adsorbents may be further modified chemically, physically, mechanically or a combination thereof. Some examples of such modifications are discussed in more detail herein.

As discussed, it is preferred to use a molecular sieve adsorbent with a pore mouth diameter greater than 4 Å. It is more preferred to have pore diameters in the range of from about 5 Å to about 8.5 Å, most preferably from about 5.3 Å to about 7 Å. Such a pore size may be achieved in several ways. For instance, ZSM-5, a medium pore size MFI type zeolite has a pore diameter of about 5.5 Å. Accordingly, there may not be any need to modify it with respect to pore diameter. Other medium pore molecular sieves suitable for use as adsorbents include, but are not limited to, borosilicate, silicalite, SAPO-11, ALPO-11, and mixtures thereof. When a ZSM-5 zeolite is used, it is more preferable to use one with a Si/Al ratio in the range of from about 40 to as high as close to infinity, provided that the material can retain the MFI type solid state structure.

Large or very large pore molecular sieves such as mordenite, zeolite X, zeolite Y may be modified chemically or by other ways, such as chemical vapor deposition, to reduce their pore diameters from over about 8.5 Å to below about 7 Å. It is also possible to enlarge the pore mouth of a small pore molecular sieve. For instance, it may be possible to use an acid, such as HCl, HF, or others to remove certain elements such as aluminum from the framework controlling the pore size. Other methods may employ electron or other high-energy beams. In this manner, small pore molecular sieves may be converted into a usable form of adsorbent for the present invention.

A molecular sieve may be further modified with metals or non-metals to improve the adsorption properties for the present invention. Such modifications may result in many different effects. If metals concentrate at the pore mouths, the pore diameter may be reduced or restricted. The metals may also assist in improving differentiations in diffusion rates (kinetics) or adsorption energetics (thermodynamics) or both. It is certainly possible that a combination of different effects may take place with a particular modification by a particular metal or metals of a particular molecular sieve.

As discussed previously, a PSA step is operated in the vapor or gas phase. In order to maintain all or substantially all of the feedstock compounds inside a PSA unit in a vapor or gaseous phase, one having ordinary skill in the art understands that there is a general correlation between operating temperature and total/partial pressures of the compounds. In general, for a given mixture composition to be separated, the higher the sorbent bed temperature is, the higher an operating pressure one may be able to use. Higher pressures are preferred for the adsorption mode of the PSA unit.

A suitable temperature in a PSA unit in the adsorption mode should be in the range of from about 150° C. to about 400° C., preferably from about 200° C. to about 375° C. It is preferred that the temperature in a PSA is not higher than that of the isomerization effluent coming out of the isomerization reactor so that no additional heat input is needed. The isomerization effluent may have to go through a heat exchanger to lower its temperature (see FIG. 1).

Temperatures lower than 150° C. or higher than 400° C. may be used to separate the xylenes with PSA in the adsorption mode. They are not preferred because there may be certain unfavorable operational or economic reasons, which may render such temperatures unattractive commercially. For instance, if a PSA unit is operated below 175° C., a vacuum (a pressure less than about 101 kPa) may be needed to desorb much of PX in the desorption mode. This may require special equipment or vacuum pumps. It may adversely affect process and/or plant designs and/or process economics.

If a PSA unit is operated at too high a temperature during adsorption, the capacity of the adsorbent may be too low to be useful even though the PSA system may be operated at a much higher pressure. Typically, the capacity of a particular adsorbent decreases with increasing operating temperature. Furthermore, if the PSA temperature is higher than the isomerization reactor temperature, additional heat input is required, resulting in higher utility expenses. Thus, the selection of a particular set of reaction conditions, particularly temperature and pressure for a particular PSA unit would need to take into account of many factors, some technical, some operational and some economical.

The pressure for the adsorption mode is in the range of from about 200 kPa to about 20 MPa, preferably from about 400 kPa to about 15 MPa. Again, higher pressure may require higher temperature in order to avoid or minimize liquid formation.

While a higher PSA temperature would allow the adsorption to be carried out at a higher pressure and still maintain all the components in a vapor phase, it is not known if any adsorbent would provide satisfactory results at a temperature higher than about 200° C. and under the conditions of the present invention. It was unexpectedly discovered that certain adsorbents could separate PX satisfactorily and effectively in a PSA unit under the disclosed conditions, particularly at the higher temperatures, of the present invention.

The adsorbent(s) in the PSA has a certain capacity under the conditions to selectively adsorb and/or otherwise retain PX from the isomerization effluent coming from the isomerization reactor. Before this capacity is reached, the exiting raffinate is a PX-depleted, fully or partially, product. In other words, the PX concentration is lower than that in the isomerization effluent coming out of the isomerization reactor.

Once the adsorbent in the PSA unit has reached or nearly reached its capacity, the flow of the feedstream is stopped, diverted to another PSA unit, bypassed to another unit such as a de-toluene tower, or a combination thereof. Exactly when the feedstream is stopped depends on many factors like economics, preferred operating mode and others. After the PSA is switched to the desorption mode, the pressure of the PSA unit is lowered to desorb PX and any other adsorbed compounds to form a desorption effluent which contains some residual hydrogen and PX in a super-equilibrium concentration, i.e. a PX concentration higher than that obtained in the isomerization effluent exiting the isomerization reactor. Typically, there is also some hydrogen in the desorption effluent. The super-equilibrium PX concentration in the desorption effluent is higher than the PX concentration in the feed to the PSA unit. In other words, the desorption effluent is PX enriched. The super-equilibrium PX concentration should be at least about 28 wt % of all the four $C_8$ aromatic compounds, preferably higher than about 30 wt % and more preferably higher than about 32 wt %.

The desorption mode is carried out at a temperature in the range of from about 150° C. to about 550° C., preferably from about 200° C. to about 500° C. The pressure in the desorption mode can be any value lower than the adsorption pressure. There is usually a blowdown step to reduce the pressure after the adsorption is completed. A useful range is from about 1 kPa to about 1 MPa, preferably from about 10 kPa to about 500 kPa, more preferably from about 101 kPa (about 0 psig or 1 atm or about ambient pressure) to about 200 kPa. Consideration is given not just for how much PX can be recovered, but also if additional pressurization would be needed for any downstream separations.

The desorption mode is completed when very little hydrocarbon still comes out of the PSA unit after depressurization. The PSA unit is re-pressurized to go through the adsorption mode again following desorption. Regardless of whether there is a purge, the total time between a complete cycle, for example from the beginning of the desorption step to the beginning of the next desorption step, is called a cycle time. As discussed earlier, the cycle time may be fixed or varied.

The cycle time selected for a process or plant depends on many factors, such as the selected adsorbent, any heat absorbing medium present, the PX concentration in the isomerization effluent, the desired super-equilibrium PX concentration in the desorption effluent, the adsorption conditions, the desorption conditions, the number of PSA and isomerization reactors in the process, the constraints imposed by other equipment or apparatus of the process and others. Typically, the cycle time suitable for the present invention is in the range of from about 0.1 sec to about 120 minutes, preferably from about 0.1 sec to about 60 minutes. As explained earlier, the short cycle times are preferred with structured sorbents. For other types of sorbents, such as pellets, granules, particles, and others, the lower limits are about one minute, preferably about two minutes.

In order to match the throughput, the flow rates of various streams or effluents and the PX production rates with different equipment sizes, it may be desirable to have more than one isomerization reactor and/or more than one adsorption unit. It is preferred to have at least two PSA units.

The preceding discussion of PSA applies in major part to TSA operations, which are known as an alternative procedure to PSA. In TSA, the cycle time is extended and the heat pulse mentioned above is allowed to proceed out of the downstream end of the adsorbent bed during the feed or on-line period. To achieve regeneration it is therefore necessary to supply heat to desorb the adsorbed component. To this end the regenerating gas used is heated for a period to produce a heat pulse moving through the bed countercurrent to the normal feed direction. This flow of heated regenerating gas is usually followed by a flow of cool regenerating gas that continues the displacement of the heat pulse through the bed toward the upstream end. TSA is characterized by an extended cycle time as compared to PSA, it differs from PSA primarily only in regards to the manner in which the absorption bed is regenerated. Hence TSA may be used in like manner as PSA is used for purposes of this invention.

The present invention also relates to a production system for producing a para-xylene enriched product, which comprises at least one xylene isomerization reactor containing an isomerization catalyst and under a hydrogen partial pressure, wherein a first para-xylene depleted feedstream is isomerized to produce a first product having para-xylene at or near an equilibrium concentration under isomerization conditions; at least one gas phase pressure-swing adsorption unit operating in a cycle to produce from the first product, alternately, a para-xylene depleted product in an adsorption mode and the para-xylene enriched product having a super-equilibrium para-xylene concentration in a desorption mode; and at least one para-xylene recovery unit wherein para-xylene is separated and recovered from the para-xylene enriched product.

It is common and sometimes preferred to have at least two isomerization reactors. The first isomerization reactor is operated at a temperature high enough to destroy as much EB (to form benzene and ethane in the presence of hydrogen) as practical while isomerizing the xylenes. The product effluent from the first isomerization unit having an equilibrium or a near equilibrium PX concentration is sent to a PSA or TSA unit operating at a lower temperature. The PX depleted and low EB exiting raffinate from the SA unit is then sent to a second isomerization reactor at about the same temperature as the SA unit itself for isomerization. The product is sent to the same SA or a different SA unit to produce a second PX-depleted exiting raffinate, which is sent back to the lower temperature second xylene isomerization reactor for further isomerization or is simply purged out the process. A second desorption effluent comprising PX enriched product from the SA unit is sent to a PX separation unit to recover pure PX.

It is also preferred to have at least two SA units with same or different adsorbents and under the same or different conditions—temperatures, pressures, cycle times, flow rates and others. Thus, it is possible to have one SA unit in the adsorption mode, the other, the desorption mode. Sometimes, it may be preferred to have a plurality of SA units in order to provide a smoother continuous production operation. An elaborate control system may be required in order to ensure the streams are directed to the intended SA unit at the right time during the cycle.

Figure 2:
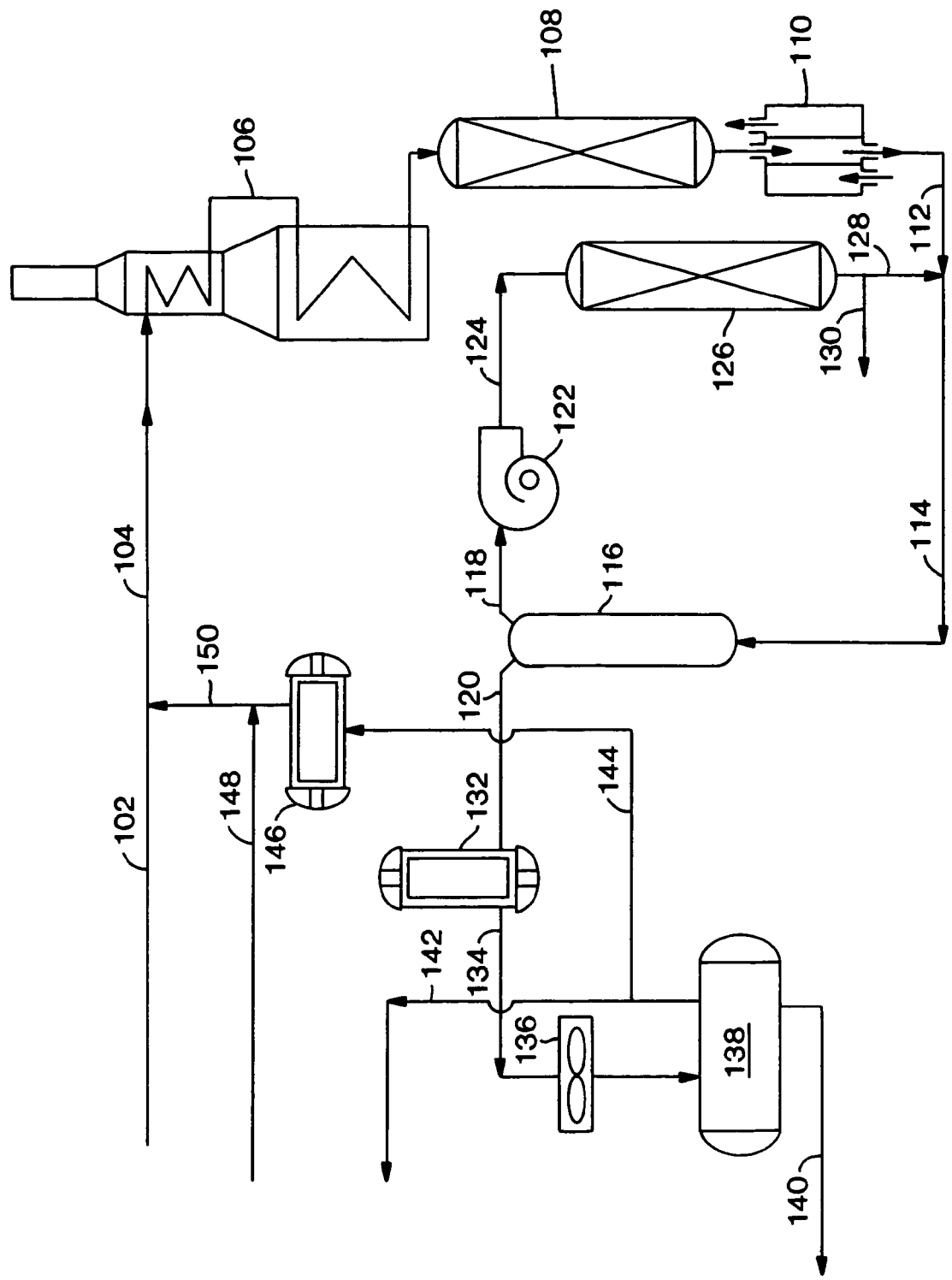
FIG. 2 depicts a schematic diagram of another process and simplified system with the associated apparatus and equipment in accordance with the present invention.

Many of the inventive features and embodiments discussed so far can be better understood by referring to FIG. 1 and FIG. 2.

In a typical and simplified process/system as depicted in FIG. 1, a PX containing $C_8$ aromatic feedstream 2 is mixed with hydrogen and a PX depleted exiting raffinate 20 (infra) and recycled hydrogen 36 from the PSA process or system. This mixture 4 passes through heat exchanger 6 to raise its temperature to a desired level before it is fed into isomerization reactor 8. There could be more than one isomerization reactor. There is usually at least one isomerization catalyst in the isomerization reactor. The effluent from 8, an isomerization effluent, passes through heat exchanger 10 to form low temperature stream 12 then through vapor (gas) phase pressure-swing adsorption unit, 14, which contains an adsorbent such as a particular molecular sieve or mixtures. The temperature in PSA unit 14 is preferably lower than that in reactor 8. There could be more than one PSA unit.

PSA unit 14 is operated in at two different modes, adsorption and desorption. In the adsorption mode, exiting raffinate 16, with fully or partially depleted PX, goes through recycle blower 18 to form high pressure raffinate 20. Raffinate 20 is mixed with feedstream 2 to become part of feedstream 4. When the capacity of the adsorbent in 14 is reached (supra for definition), PSA unit 14 switches to a desorption (blowdown) mode. The flow of stream 12 is stopped, bypassed to a different unit such a de-toluene tower, or when more than one PSA unit is used, diverted to another PSA unit (not shown in FIG. 1). During the desorption mode, the pressure in PSA unit 14 is lowered in a blowdown step followed by a desorption step.

Desorption effluent 22 containing hydrogen and a product having PX in a super-equilibrium concentration is fed into compressor 24 to form high pressure stream 26, which is sent to a recovery drum 30 after first going through gas-liquid separator 28. Liquids 32 from the recovery drum are sent for PX and benzene separation and recovery. Gas 34 is used for hydrogen recycle stream 36 or purged through 38. Some purge of hydrogen from the system is needed in order to prevent hydrogen buildup in the process. Recycle stream 36 goes through compressor 40, mixes with make-up hydrogen 42, if any is needed, and then recycles back to become part of feedstream 2.

After the desorption mode is completed, flow of stream 12 to PSA unit 14 is resumed to begin the adsorption mode again. There may be additional purge(s) before, during, or after each mode of the entire cycle. The time to complete one entire cycle, including any purges, is called a cycle time.

In another simplified process/system as depicted in FIG. 2, a PX containing $C_8$ aromatic feedstream 102 is mixed with hydrogen 150 from make-up hydrogen 148 and any recycled hydrogen 144. This mixture 104 passes through heat exchanger 106 to raise its temperature to a desired level before it is fed into a first xylene isomerization reactor 108. The temperature is high enough to destroy much EB in the feedstream during isomerization. There is at least one isomerization catalyst in 108. The effluent from 108, an isomerization effluent, passes through heat exchanger 110 to form stream 112. Stream 112 is mixed with stream 128 (infra) to form stream 114 as a feed to vapor (gas) phase pressure-swing adsorption unit, 116, which contains an adsorbent such as a particular molecular sieve or mixtures. The temperature in PSA unit 116 is preferably lower than that in reactor 108.

PSA unit 116 is operated in at two different modes, adsorption and desorption. During the adsorption mode, exiting raffinate 118, containing some hydrogen and with PX fully or partially depleted, goes through recycle blower 122 to form high pressure raffinate 124. Raffinate 124 is fed into a second xylene isomerization reactor 126, which operates at a temperature lower than that of reactor 108. The second isomerization effluent 128 may either be mixed with stream 112 or otherwise recovered as stream 130.

When the capacity of the adsorbent in 116 is fully or nearly fully used up, PSA unit 116 switches to a desorption mode with a blowdown step and a desorption step. The flow of stream 114 is stopped, bypassed to a different unit such as a de-toluene tower, or when more than one PSA unit is used, diverted to another PSA unit (not shown in FIG. 2). During this desorption mode, the pressure in PSA unit 116 is lowered. Desorption effluent 120 containing residual hydrogen and a PX enriched product having PX in a super-equilibrium concentration is fed into compressor 132 to form high pressure stream 134, which is sent to a recovery drum 138 after first going through gas-liquid separator 136. Liquids 140 from the recovery drum are sent to a separator (not shown) for PX and benzene separation and recovery. Gas 142 is purged. Some purge of hydrogen from the system is needed in order to prevent hydrogen buildup in the process. Optionally, a part of the gas 144 is sent to compressor 146 and the higher pressure exiting gas from 146 is mixed with makeup hydrogen stream 148 to become stream 150. After the desorption mode is completed, flow of stream 114 to PSA unit 116 is resumed to begin the adsorption mode again.

Figure 3:
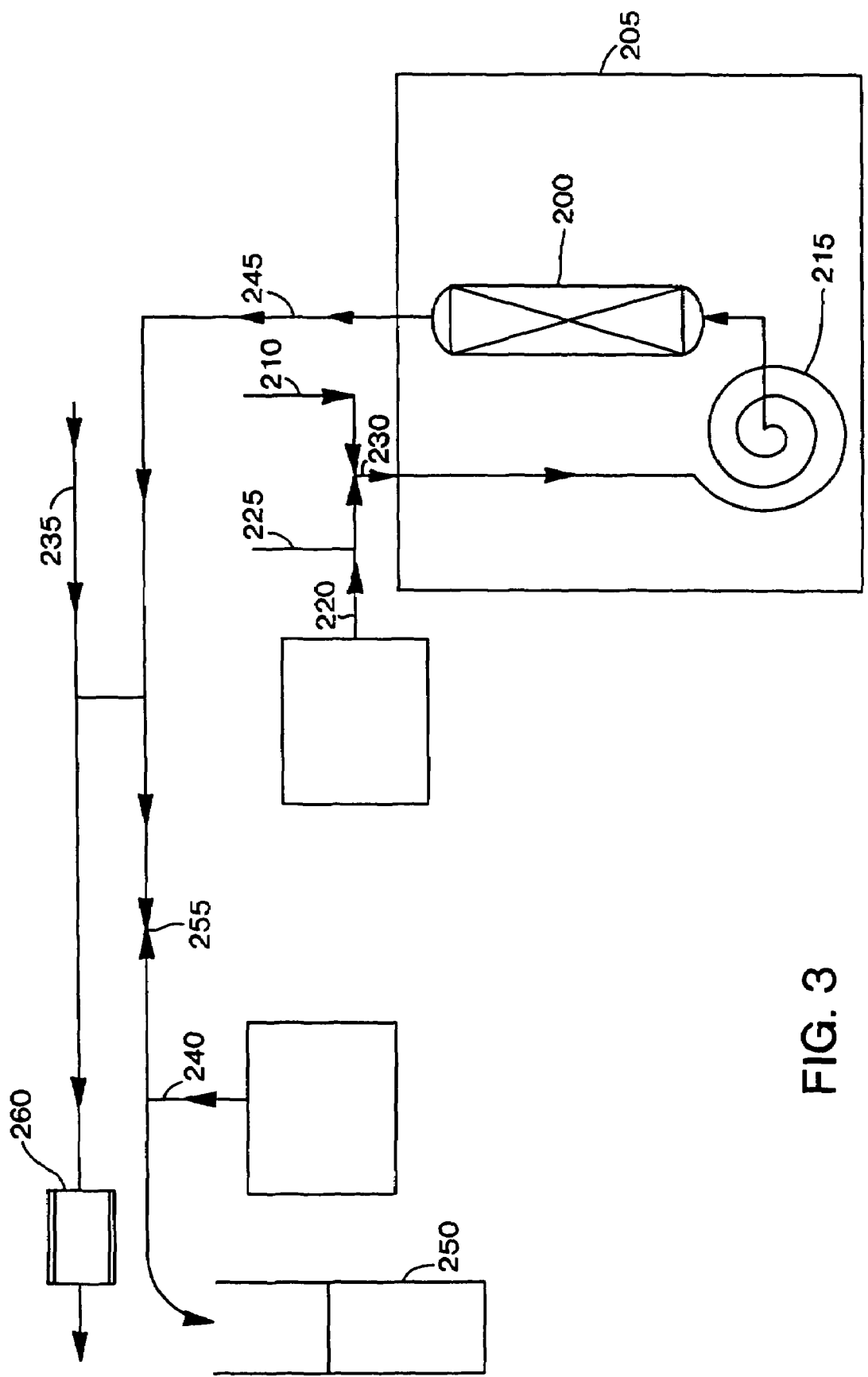
FIG. 3 is a simple diagram of the equipment used for carrying out the adsorption experiments.

The following competitive adsorption experiments with synthetic mixtures are used to further illustrate that under the disclosed conditions, PX can be effectively and selectively separated from MX and EB. A product with PX in a super-equilibrium concentration is formed by using an MFI type zeolite, S115, silicalite as the adsorbent. As discussed earlier, MFI type zeolites have 10-membered ring pores with a typically described medium-pore size, about 5.5 Å. The experimental equipment is shown in FIG. 3.

The experiments were carried out as follows: a sample of pre-calcined zeolite was weighed and loaded into a 10 ml sorbent bed 200, which was placed in sand bath 205 for controlling the temperature. Hydrogen gas 210 was introduced into the sorbent bed through a preheater coil 215 through the proper use of a three way valve 230 and the temperature of the sorbent bed was raised to about the desired experimental temperature which can be in the range of 150° C. to 350° C., such as 300° C. The pressure in the sorbent bed was raised to the desired pressure with hydrogen 235 by using and adjusting a back-pressure regulator 260 installed downstream from the reactor. The aromatic compounds 220 and, in certain experiments, hydrogen 225 were introduced into the reactor at a preset rate—usually in the range of from about 0.05 ml/min to about 0.5 ml/min of aromatics through the proper use of a three way valve 230. As products 245 exiting from the adsorber, a product was collected in sample collection vial 250 at a preset interval, typically from 30 to 60 seconds through the proper use of a metering valve 255. Hexane, 240, at a constant flow rate of about 0.5 ml/min, was pumped into the products 245 continuously to serve as a reference compound (marker) for product analysis. The products were analyzed at predetermined intervals with n-hexane as a reference compound (marker) by using a gas chromatograph equipped with a flame ionization detector (FID). The analytical instrument and any associated equipment are not shown in the drawing.

In the following set of experiments, the adsorption temperature was set at 250° C.; pressure 240 kPa (about 50 psig); flow rate of the liquid aromatic feeds stream, 0.085 cc/min; and the adsorbent, S115 MFI zeolite powder. This adsorbent was a commercial material obtained from Union Carbide Corporation and had a Si/Al ratio greater than about 400. The aromatic feed used in these experiments had the following composition: 5 wt % EB, 20 wt % PX, 70 wt % MX, and 5 wt % 1,3,5-trimethylbenzene.

Figure 4:
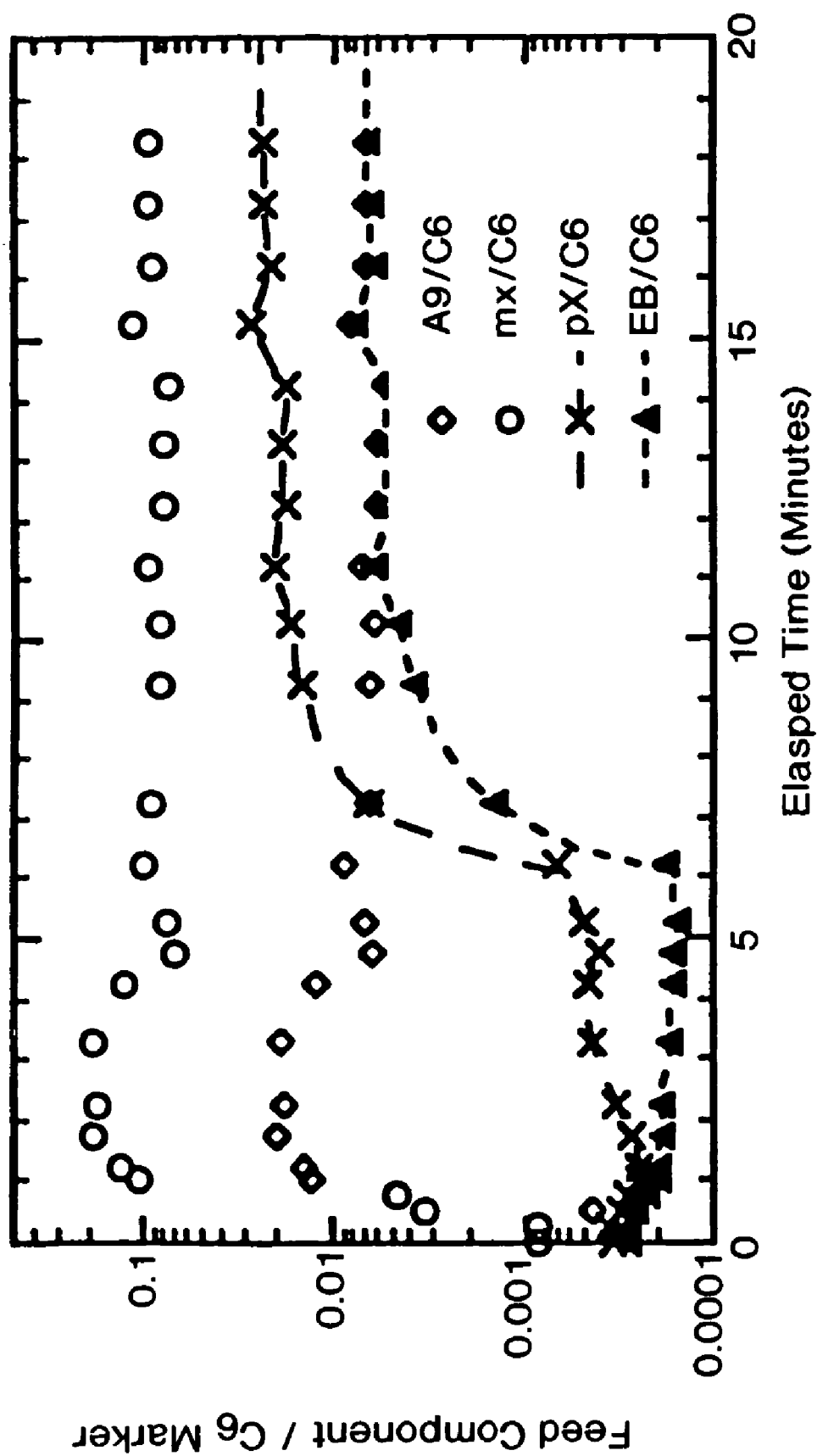
FIG. 4 shows the results of different competitive adsorption experiments described herein. The concentrations of PX, MX, EB and TMB, detected in the effluent and relative to an n-hexane standard by using a gas chromatograph equipped with a flame ionization detector, FID, are plotted as a function of time. TMB is 1,3,5-trimethylbenzene, a $C_9$ aromatic compound.

The results are shown in FIG. 4. The amounts of PX, MX, EB, and TMB (all relative to an analysis marker, n-hexane) measured in the effluent, the vertical coordinate, are plotted against time, the horizontal coordinate. It can be seen that PX was largely retained by the adsorbent and very little was detected in the effluent until about 6 to 7 minutes into the adsorption experiment. This part of the experiments would represent or simulate the adsorption mode of a PSA unit in a plant operation. The effluent here would parallel PX detected in an exiting raffinate from a PSA unit. In contrast, MX was not adsorbed by the adsorbent to any significant extent. The MX concentration in the effluent was about the same as that in the feed. It is estimated from FIG. 4 that, during this about ten-minute period of effective adsorption of PX, the PX/MX selectivity was about 4.5. In a similar manner, it is noticed from FIG. 4 that EB also disappeared from the feed during the same period when PX was adsorbed. The PX/EB selectivity in these experiments was about 2. As evidenced by the concentrations detected in the effluent, the heavier $C_9$ compound, TMB, was not adsorbed by the S115 MFI zeolite in these experiments.

While a number of theories or theoretical aspects have been presented and discussed, the present invention is neither limited nor intended to be limited by any particular theory cited or discussed herein. The theories are intended only for easier understanding and better appreciation of the disclosed invention. Similarly, the examples are intended for illustration purposes only. The theories and the examples should not be interpreted to limit the spirit or the scope of the present invention, which is defined by the written description and the following claims.

The invention claimed is:

1. A para-xylene production system for producing a para-xylene enriched product, which comprises:
   at least one xylene isomerization reactor containing an isomerization catalyst and under a hydrogen partial pressure, wherein a feedstream comprises xylenes and ethylbenzene and the ethylbenzene is at least partially isomerized and/or at least partially destroyed and the xylenes is isomerized to produce a first product having para-xylene at or near an equilibrium concentration under isomerization conditions;
   at least one vapor phase swing adsorption unit operating in a cycle to produce from the first product, alternately, a para-xylene depleted product in an adsorption mode and the para-xylene enriched product having a super-equilibrium para-xylene concentration in a desorption mode; and
   at least one para-xylene recovery unit wherein para-xylene is separated and recovered from the para-xylene enriched product.

2. The system recited in claim 1, wherein said at least one vapor phase swing adsorption unit contains a sorbent.

3. The system recited in claim 2, wherein said sorbent is selected from the group consisting of carbon, a zeolite having a pore diameter of from about 5 Å to about 8.5 Å, and mixtures thereof.

4. The system recited in claim 2, wherein said sorbent comprises ZSM-5, borosilicate, silicalite, SAPO-11, ALPO-11 and mixtures thereof.

5. The system recited in claim 4, wherein said sorbent is ZSM-5.

6. The system recited in claim 1, wherein said at least one vapor phase swing adsorption unit is a pressure swing absorption unit.

7. The system recited in claim 1, wherein said at least one vapor phase swing adsorption unit is a temperature swing absorption unit.

8. A para-xylene production system for producing a para-xylene enriched product, which comprises:
   at least one first xylene isomerization reactor containing a first catalyst and at a first temperature under a first hydrogen partial pressure, wherein a feedstream comprising xylenes and ethylbenzene is isomerized to produce a first product having para-xylene at or near a first equilibrium concentration under first isomerization conditions;
   at least one vapor phase swing adsorption unit operating in a cycle to produce from the first product, alternately, a para-xylene depleted product in an adsorption mode and the para-xylene enriched product having a super-equilibrium para-xylene concentration in a desorption mode;
   at least one second xylene isomerization reactor containing a second catalyst and at a second temperature and under a second hydrogen partial pressure, wherein the second temperature is lower than the first temperature and a second product having para-xylene at or near a second equilibrium concentration under second isomerization conditions from the para-xylene depleted product wherein the second product is sent back to the at least one vapor phase swing adsorption unit; and
   at least one para-xylene recovery unit wherein para-xylene is separated and recovered from the para-xylene enriched product.

9. The system recited in claim 8, wherein said at least one swing adsorption unit contains a sorbent.

10. The system recited in claim 9, wherein said sorbent is selected form the group consisting of carbon, a zeolite having a pore diameter of from about 5 Å to about 8.5 Å, and mixtures thereof.

11. The system recited in claim 9, wherein said sorbent comprises ZSM-5, borosilicate, silicalite, SAPO-11, ALPO-11 and mixtures thereof.

12. The system recited in claim 11, wherein said sorbent is ZSM-5.

13. The system recited in claim 8, wherein said at least one vapor phase swing adsorption unit is a pressure swing absorption unit.

14. The system recited in claim 8, wherein said at least one vapor phase swing adsorption unit is a temperature swing absorption unit.

* * * * *